US00PP26827P2

(12) United States Plant Patent
Avent

(10) Patent No.: US PP26,827 P2
(45) Date of Patent: Jun. 14, 2016

(54) ***BAPTISIA* PLANT NAMED 'IVORY TOWERS'**

(50) Latin Name: ***Baptisia* hybrid**
Varietal Denomination: Ivory Towers

(71) Applicant: Tony Avent, Raleigh, NC (US)

(72) Inventor: Tony Avent, Raleigh, NC (US)

( * ) Notice: Subject to any disclaimer, the term of this patent is extended or adjusted under 35 U.S.C. 154(b) by 121 days.

(21) Appl. No.: 14/121,411

(22) Filed: Sep. 2, 2014

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
(74) *Attorney, Agent, or Firm* — Penny J. Aguirre

(57) ABSTRACT

A new cultivar of interspecific *Baptisia*, 'Ivory Tower', that is characterized by its numerous flowers that are ivory white in color, its tall plant habit; reaching 1.5 m in height, its dark grey-purple flower stems until daytime temps consistently reach 80° F. and above (early May in Raleigh, N.C.), its flower stems that rise up to 75 cm above the foliage canopy, and its excellent hybrid vigor.

2 Drawing Sheets

Botanical classification: *Baptisia* hybrid.
Cultivar designation: 'Ivory Towers'.

BACKGROUND OF THE INVENTION

The present invention relates to a new and distinct cultivar of hybrid *Baptisia* plant, botanically known as *Baptisia* 'Ivory Towers' and will be referred to hereafter by its cultivar name, 'Ivory Towers'. The new cultivar represents a new false indigo, an herbaceous perennial grown for landscape use.

The new invention arose from an ongoing breeding program by the Inventor in Raleigh, N.C. The objective of the breeding program is to develop novel interspecific hybrids of *Baptisia* that exhibit good garden performance with tall and upright plant habits and inflorescences that are held well above the foliage.

'Ivory Towers' originated as a seedling that arose from seed planted from open pollination of an unnamed plant from the Inventors breeding program of *Baptisia albescens*, accession no. A7NC-016 (not patented), in April of 2003 in a controlled block of potential pod and seed parents. The male parent unknown, however it is thought to be a plant of *Baptisia alba* based on the characteristics of the new cultivar. The new *Baptisia* was selected as a single unique plant in May of 2011.

Asexual propagation of the new cultivar was first accomplished by shoot tip cuttings in May of 2009 in Raleigh, N.C. under the direction of the Inventor. Asexual propagation by shoot tip cuttings has determined that the characteristics of the new cultivar are stable and are reproduced true to type in successive generations.

SUMMARY OF THE INVENTION

The following traits have been repeatedly observed and represent the characteristics of the new cultivar as observed in Raleigh, N.C. These attributes in combination distinguish 'Ivory Towers' as a unique cultivar of *Baptisia*.

1. 'Ivory Towers' exhibits numerous flowers that are ivory white in color.

2. 'Ivory Towers' exhibits a tall plant habit; reaching 1.5 m in height.
3. 'Ivory Towers' exhibits dark grey-purple flower stems until daytime temps consistently reach 80° F. and above (early May in Raleigh, N.C.).
4. 'Ivory Towers' exhibits flower stems that rise up to 75 cm above the foliage canopy.
5. 'Ivory Towers' exhibits excellent hybrid vigor.

The female parent of 'Ivory Towers' differs from 'Ivory Towers' in having much smaller flowers with greater internode lengths between flowers, thinner flowering stems that are lighter in color, and in having a less dense plant habit. 'Ivory Towers' can be most closely compared to *Baptisia* cultivars 'Wayne's World' (not patented) and 'Lunar Eclipse' (U.S. Plant Pat. No. 25,875). 'Wayne's World' is similar to 'Ivory Towers' in overall plant habit, blooming period, and flower color. 'Wayne's World' differs from 'Ivory Towers' in having fewer flowering stems that are lighter in color, in being about 30 cm shorter in height, and in having a less vigorous plant habit. 'Lunar Eclipse' is similar to 'Ivory Towers' in flower color and season of bloom. 'Lunar Eclipse' differs from 'Ivory Towers' and in having flowers that age to a blue color and in having fewer flowering stems that are lighter in color.

BRIEF DESCRIPTION OF THE DRAWINGS

The accompanying colored photographs illustrate the overall appearance and distinct characteristics of the new *Baptisia*. The photographs were taken of plants nine years in age as grown outdoors in a trial garden in Raleigh, N.C.

The photograph in FIG. 1 provides a side view of 'Ivory Towers' in bloom and illustrates its plant habit and numerous flowering stems.

Figure 1:
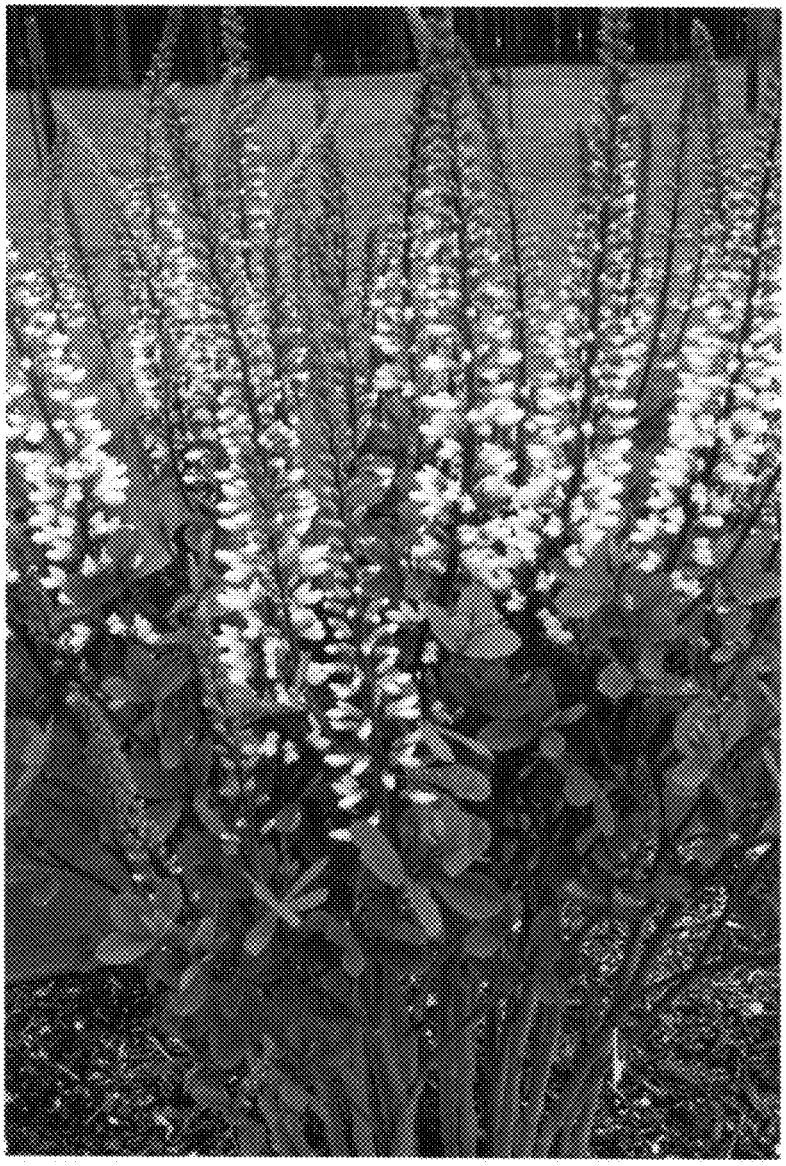
Figure 2:
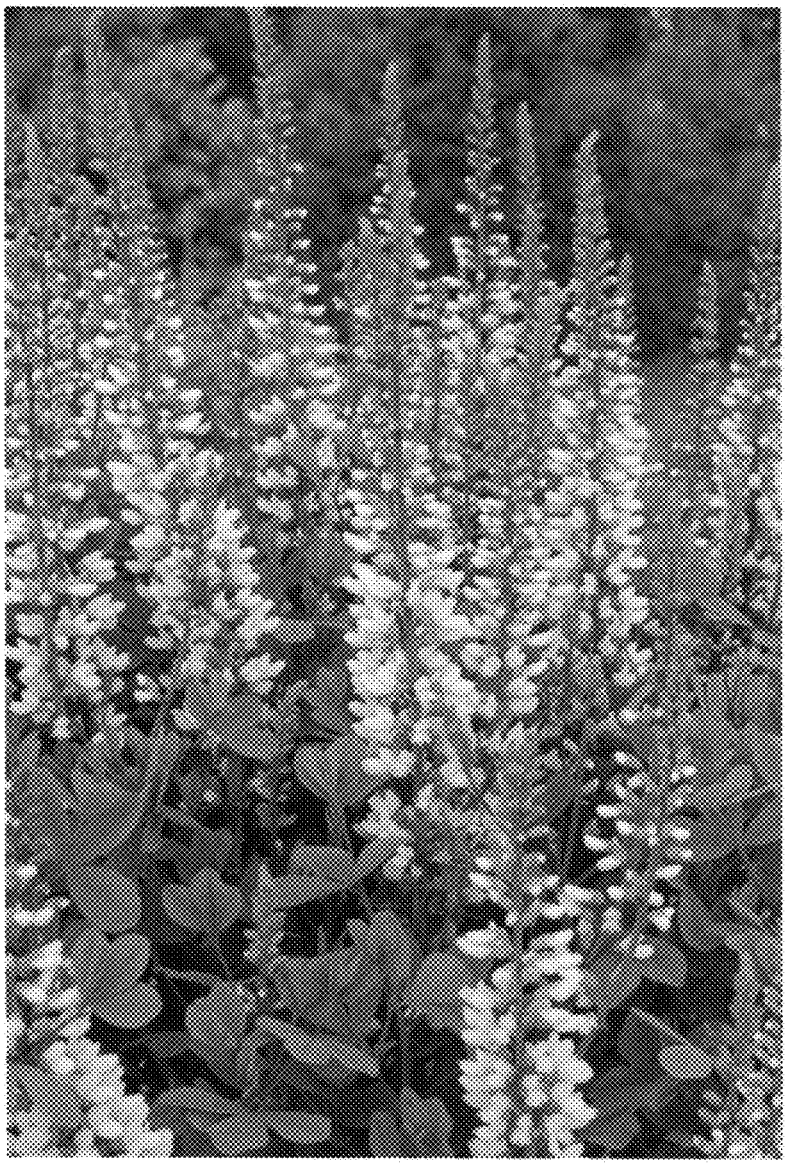

The photograph in FIG. 2 is provides a close-up view of the inflorescences.

The colors in the photographs are as close as possible with the photographic and printing technology utilized and he color values cited in the detailed botanical description accurately describe the colors of the new *Baptisia*.

DETAILED BOTANICAL DESCRIPTION OF THE PLANT

The following is a detailed description of ten year-old plants of the new cultivar as grown outdoors in a trial garden in Raleigh, N.C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Late April to mid May in Raleigh, N.C.

*Plant habit*.—Upright and dense with flowering stems held up to 75 cm above the foliage canopy.

*Height and spread*.—An average of 1.5 m in height and spread.

*Hardiness*.—At least in U.S.D.A. Zones 4 to 9.

*Diseases*.—No susceptibility to disease has been observed.

*Root description*.—Deep rooted, fleshy.

*Propagation*.—Shoot tip cuttings.

*Growth rate*.—Vigorous.

Stem description:

*Branch habit*.—Densely branched; average of 52 branches, each with an average of 3 secondary branches, and 2 tertiary branches.

*Stem size*.—Main stem; average of 1.5 m (including peduncle) in length and 1.8 cm in width, secondary; average of 97 cm in length and 9 mm, tertiary; an average of 45 cm in length and 3.5 mm in width.

*Stem shape*.—Oval.

*Stem color*.—144A and suffused with N187A and changes to 144A when temperatures consistently reach 80° F. and above (early May in Raleigh, N.C.), a blend of 200A and N200C when seedpods are present.

*Stem surface*.—Glabrous, satiny, glaucous with ridges.

Foliage description:

*Leaf shape*.—Fan-shaped in overall outline.

*Leaf division*.—Ternate.

*Leaf internode*.—Foliage begins about 82 cm from base until foliage expands, an average of 10 cm on main stem and an average of 7 cm on secondary branches.

*Leaf size*.—Average 5.5 cm in length and 8 cm in width when mature.

*Leaf quantity*.—About 10 per stem.

*Leaflet shape*.—Obovate to oval.

*Leaflet base*.—Cuneate.

*Leaflet apex*.—Retuse.

*Leaflet venation*.—Pinnate pattern, not conspicuous, color matches leaflet color on the upper and lower surface with the mid rib of lower surface 143C.

*Leaflet margins*.—Entire.

*Leaf attachment*.—Petiolate.

*Leaf arrangement*.—Alternate.

*Leaflet surface*.—Glabrous and slightly glaucous on upper and lower surface.

*Leaflet color*.—Newly expanded; upper and lower surface 144A to 144B, mature; upper surface a blend of 137A and 138A and lower surface 137C.

*Leaflet size*.—An average of 5 cm in length and 3 cm in width.

*Petioles*.—Average of 1.3 cm in length and 1.5 mm in width, clasping to stem at mature nodes, 144A in color, surface is glabrous and satiny.

*Stipules*.—Absent.

Flower description:

*Inflorescence type*.—Terminal racemes of pea-like flowers on main and secondary branches, blooms from the base to the apex.

*Inflorescence size*.—Average of 75 cm in length and 5 cm in width at mid stem.

*Lastingness of inflorescence*.—About 20 days.

*Flower size*.—An average of 2.5 cm in length and about 1.3 cm in diameter.

*Flower fragrance*.—None detected.

*Flower number per inflorescence*.—About 90.

*Peduncle*.—Rounded in shape, up to 75 cm in length and an average of 5 mm in width, 144A in color and suffused with N187A and changes to 144A when temperatures consistently reach 80° F. and above (early May in Raleigh, N.C.), surface is glabrous, satiny, and glaucous with ridges, flower internode length averages 1 cm.

*Petiole*.—About 7 mm in length, about 1 mm in width, rounded in shape, 143A in color, glabrous and satiny surface.

*Flower buds*.—Kidney-shaped, about 1.9 cm in length and 7 mm in width, petal portion is N155C in color and suffused with 145C, calyx portion same as open flowers.

*Flower type*.—Papilionaceous, held at about a 45° angle.

*Calyx*.—Campanulate, about 8 mm in length and 5 mm in diameter, surface is glabrous and dull, persistent.

*Sepals*.—5, fused with the exception of apex of each, free portion is triangular in shape, 2.5 mm in width and 3 mm in depth with an acute apex, color 146B and slightly suffused with N187A, surface is glabrous on both surfaces.

*Corolla features*.—Papilionaceous (4 segments) with a moderately reflexed banner, 2 lateral wings and a concealed keel, lateral wings; oblong (slightly oblique) in shape, about 1.7 cm in length and 4 mm in width, color on outer surface and the inner surface is NN155C and 145D near base, rounded apex, oblique base, keel; not visible, comprised of 2 segments surrounding reproductive organs, oblong (slightly oblique) in shape with rounded apex and oblique base, 1.5 cm in length and 5 mm in width, upper surface and lower surface are a blend of 157A and 145D in color, segments joined at center point, banner; orbicular in shape with rounded, about 1.8 cm in length and 1 cm in width, color on outer surface is NN155C with center on lower center portion 145C and markings of 166A in center, color of the inner surface is NN155C with lower center portion a blend of 145B and 145C, apex is rounded with a single notch, surface is glabrous on all sections.

*Receptacle*.—Disk-shaped, gelatinous, 145A in color, about 1.5 mm in diameter and depth.

Reproductive organs:

*Gynoecium*.—1 Pistil, about 1.3 cm in length, 1 mm in width; style is 145B in color and 4 mm in length; stigma minute, too small to read color, ovary is superior with a stipe, 145A in color, 5 mm in length and 1.5 mm in width; stipe is 145B in color, 2.5 mm in length and 1 mm in width.

*Androcoecium*.—10 stamens, not united, 1.8 cm in length and 1 mm in width; filament is 1 cm in length, 1 mm in width and 145D in color; anther is dorsifixed, 2 mm in length and 1 mm in width and 161B in color, pollen is moderate in quantity and 17A in color.

*Fruit*.—An inflated pod, technically a legume, average of 29 produced per inflorescence, irregularly oblong in shape with one more flattened side, average of 3 cm in length by 2 cm in width with beak an average 5 mm in length and curled, color of outer surface when mature is a blend of 200A and 202B, color of inner surface when mature is a blend of N199A and 200A, walls 1.5 mm and hard at maturity, seed; average of 15 per fruit, N199C in color, oval with the hilum side more or less straight, 5 mm in length, 3.5 mm in width and 2 mm in thickness.

It is claimed:

1. A new and distinct cultivar of *Baptisia* plant named 'Ivory Tower' as herein illustrated and described.

* * * * *